United States Patent [19]

Thiel et al.

[11] 4,058,565
[45] Nov. 15, 1977

[54] PROCESS FOR OXIDIZING HYDROCARBONS

[75] Inventors: Reinhard Thiel; Heinz Jörg Rosenbaum, both of Krefeld, Germany

[73] Assignee: Bayer Aktiengesellschaft, Leverkusen, Germany

[21] Appl. No.: 676,605

[22] Filed: Apr. 13, 1976

Related U.S. Application Data

[63] Continuation of Ser. No. 411,525, Oct. 31, 1973, abandoned.

[30] Foreign Application Priority Data

Dec. 8, 1972 Germany .............................. 2260114

[51] Int. Cl.$^2$ ...................... C07C 27/12; C07C 27/26; C07C 29/00; C07C 45/02
[52] U.S. Cl. .......................... 260/586 AB; 260/462 A; 260/597 R; 260/617 H; 260/631 B; 260/632 CB
[58] Field of Search ........ 260/586 AB, 631 B, 462 A, 260/617 H, 597 R, 632 CB

[56] References Cited

U.S. PATENT DOCUMENTS

| | | | |
|---|---|---|---|
| 3,232,704 | 2/1966 | Helbig et al. ................. | 260/586 AB |
| 3,287,423 | 11/1966 | Stuman et al. ................. | 260/586 AB |
| 3,316,302 | 4/1967 | Stuman et al. ................. | 260/586 AB |
| 3,420,897 | 1/1969 | Russell et al. ................. | 260/586 AB |
| 3,456,021 | 7/1969 | Winnick et al. ............. | 260/586 AB |
| 3,475,500 | 10/1969 | Russell .......................... | 260/586 AB |
| 3,651,153 | 3/1972 | Strauss et al. ................. | 260/586 AB |
| 3,796,761 | 3/1974 | Marcell et al. ................. | 260/586 AB |
| 3,895,067 | 7/1975 | Mock et al. .................... | 260/586 AB |

*Primary Examiner*—Norman Morgenstern
*Attorney, Agent, or Firm*—Burgess, Dinklage & Sprung

[57] ABSTRACT

Hydrocarbons containing 4 to 20 carbon atoms are oxidized by a process which includes the following steps:
a. Reacting the hydrocarbons with a gas containing molecular oxygen in the presence of a boron compound;
b. hydrolyzing the resulting reaction mixture which contains at least one boric acid ester with an aqueous medium containing boric acid;
c. separating the hydrolyzate into a substantially organic component from which the oxidation product is recovered and a substantially aqueous component containing boric acid and water-soluble organic secondary products;
d. recovering boric acid from the aqueous component;
e. oxidizing the residual boric acid mother liquor from (d), or a part thereof in the liquid phase with a gas containing molecular oxygen; and
f. returning the resulting solution from (e) to hydrolysis step (b).

7 Claims, 2 Drawing Figures

PROCESS FOR OXIDIZING HYDROCARBONS

This is a continuation of application Ser. No. 411,525, filed Oct. 31, 1973 now abandoned.

BACKGROUND

The invention relates to a process for the oxidation of hydrocarbons.

More particularly, the invention relates to a process for the oxidation of hydrocarbons with gases containing molecular oxygen and in the presence of boron compounds to form the corresponding alcohol/ketone mixtures. More particularly, the invention relates to a process in which the boron compounds used are completely recovered and reused and water-soluble organic secondary products are eliminated by oxidation.

Hydrocarbons can be oxidized with gases containing molecular oxygen. Of considerable technical significance is the oxidation to form alcohols which, to increase selectivity, are esterified by conventional methods with boron compounds as described, for example, in U.S. Pat. No. 3,243,449.

Typical boron compounds used in oxidation processes of this kind include boric acids such as, for example, orthoboric and metaboric acid, boric acid esters such as, for example, the mono esters of metaboric acid with the alcohol of the hydrocarbon to be oxidized, for example cyclohexylmetaborate when cyclohexane is the starting material, and boric acid anhydrides such as, for example, $B_2O_3$ and $B_4O_5$. Mixtures of these boron compounds can also be used.

Recovery of the boron compound used is of considerable importance to the economy of this process. This is normally effected by hydrolysing the alcohol-boric acid ester with water to form the corresponding alcohol and orthoboric acid. Following separation of the organic phase, consisting of unreacted hydrocarbon, the alcohol and small quantities of by-products, the orthoboric acid present in the aqueous phase is recrystallized by distilling off water and/or by cooling and, after filtration and washing, is converted into the boron compound suitable for the oxidation process. The residual "boric acid mother liquor" is reused together with fresh water for hydrolysis.

Water-soluble by-products of the oxidation process such as, for example, alcohols, carboxylic acids and hydroxy carboxylic acids, accumulate in this mother liquor. They prevent crystallization of the boric acid and rapidly reduce the yield because they are recycled to the oxidation process with the crystallized boric acid (cf. DOS No. 1,618,514). To prevent this, the concentration of organic by-products in the boric acid mother liquor has to be kept within reasonable limits. This is done by continuously separating and discarding part of the boric acid mother liquor. This is inevitably accompanied by the loss of the quantity of boric acid present in the separated component of the mother liquor which has to be replaced by introducing fresh boron compound. Accordingly, substantially quantitative recovery of this boric acid is desirable and, moreover, necessary for reasons of pollution control.

Hitherto, two processes have been proposed for this purpose:

1. Another crystallization stage is employed in which the mother liquor is reconcentrated. Approximately 70% of the boric acid present in the mother liquor crystallizes out on cooling. This component is returned to the first crystallization stage after filtration and washing for the purposes of recrystallization. This post-crystallization process is described in DOS Nos. 1,618,514 and 1,768,839.

2. The second process for avoiding losses of boric acid, described in Belgian Pat. No. 783,255, is distinguished by the fact that a component stream of the hydrolysis water circuit is freed from organic impurities by extraction with a mixture essentially containing alcohols and ketones, and the extracted hydrolysis water is returned to the hydrolysis water circuit.

Unfortunately, at least 30% of the boric acid is also dissolved both physically and chemically through complex formation in the extractant. This quantity of boric acid cannot be recovered.

Both the aforementioned processes for treating boric acid mother liquor are attended by the disadvantage that a maximum of only 70% of the boric acid can be recovered. In addition, they are unsatisfactory insofar as they do not solve the problem of ultimately eliminating the large quantities of organic secondary products present in the mother liquor, which represents a pollution hazard.

SUMMARY

A process has now surprisingly been found by which it is possible to obtain complete recovery of the boric acid and, at the same time, to eilminate the organic constituents present in the boric acid mother liquor described above. Accordingly, the invention relates to a process for the oxidation of hydrocarbons, in the course of which the boric acid mother liquor is purified by wet oxidation of the organic impurities into essentially $CO_2$ and water, by treating the boric acid mother liquor with gases containing molecular oxygen at elevated temperature and pressure.

Accordingly, the invention provides a process for oxidising a $C_4$- to $C_{20}$- hydrocarbon, in which (a) the hydrocarbon is reacted with a gas comprising molecular oxygen in the presence of boron compounds; (b) the resulting reaction mixture, containing the boric acid esters, is hydrolysed by an aqueous medium containing boric acid; (c) the hydrolyzate is separated into a substantially organic phase, from which the required oxidation product is recovered, and into a substantially aqueous phase containing boric acid and one or more water-soluble organic by-products; (d) boric acid is recovered from the aqueous phase; (e) the residual boric acid mother liquor from (d), or a part thereof is oxidized in the liquid-phase with a gas comprising molecular oxygen; and (f) the resulting solution is recycled to the hydrolysis medium step (b). The gas for oxidation of the boric acid mother liquor preferably contains oxygen, in at least stoichiometric quantities sufficient for burning all the organic impurities in a reaction zone heated to at least 200° C under a pressure which is sufficient to keep at least some of the water in the liquid phase. The resulting solution, containing boric acid, is recycled to the hydrolysis stream, optionally following the removal of any solids formed by filtration.

DESCRIPTION

Hydrocarbons suitable for use in this oxidation process include saturated, linear, branched or cyclic hydrocarbons containing 4 to 20 carbon atoms per molecule such as, for example, cyclopentane, cyclohexane, methylcyclohexane, cycloheptane, dimethylcyclohexane, cyclododecane, n-butane, n-pentane, n-hexane, $C_{12}-C_{14}$- petroleum naphthane, octadecane, nonadecane and eicosane. The process can advantageously be used for oxidizing hydrocarbons containing from 5 to 12 carbon atoms and, with particular advantage, for oxidizing cyclohexane and cyclododecane into a corresponding alcohol/ketone mixture. The starting product does not have to be completely free from unsaturated substances (for example cyclohexene in the case of cyclohexane) for the process, providing it consists of more than 95 mol % of saturated hydrocarbons.

It is surprising that the boric acid mother liquor contaminated by mono-, di- and hydroxy-carboxylic acids and by alcohols can be purified by oxidation in the liquid phase to such an extent that complete recirculation of the mother liquor and, hence, complete recovery of the boric acid are possible. It is known that brown, tar-like products are formed, particularly at elevated temperatures, when boric acid mother liquor comes into contact for a while with air. Accordingly, troublesome resin formation had been expected under the wet-oxidation conditions. Although this does in fact occur, it can nevertheless be almost completely avoided, quite unexpectedly, by carrying out wet-oxidation in a reactor with complete readmixture and oxidizing the impurities in this reaction stage to an extent equivalent to at least 60% and preferably to from 70 and 80%. If desired, further degradation can subsequently be carried out in one or more following reaction stages. The very small solids component, if any, accumulating with the end liquor in this embodiment of the process according to the invention is in the form of a powder, does not stick and, if desired, can readily be removed by filtration.

DESCRIPTION OF THE DRAWING

The present invention will be more fully understood from the following description taken in conjunction with the accompanying drawing wherein:

The process according to the invention is diagrammatically illustrated in the accompanying drawing. In FIG. 1 the hydrocarbon to be oxidized, for example cyclohexane, the boron compound, for example metaboric acid, and an oxygen-containing gas, for example air, are introduced into the reaction zone 2 through the pipe 1 and reacted therein. THe exhaust gas is let off through pipe 3. The reaction mixture is brought into contact with an aqueous hydrolysis stream 5 in the hydrolysis zone 4. The boric acid esters formed in 2 decompose into the corresponding alcohols and boric acid. The hydrolysis mixture flows into the container 6 for phase separation. The organic phase is discharged through pipe 7 and worked up to recover the alcohol/ketone mixture. The aqueous phase, containing the orthoboric acid and water-soluble, organic secondary reaction products, is introduced through pipe S into the crystallization zone 9. The solid boric acid which accumulates in the crystallization zone is separated 10 and returned as auxiliary substance to the oxidation zone after suitable treatment, for example dehydratization into metaboric acid. The boric acid mother liquor, freed from boric acid crystals which accumulate in the crystallization zone 9, is returned to the hydrolysis zone 4 as hydrolysis stream 5. In order, according to the invention, to prevent the water-soluble organic secondary products from accumulating in the boric acid mother liquor, a component stream 11 is introduced into the wet-oxidation zone 12 where it is brought into contact with an oxygen-containing gas, for example air, introduced through pipe 13, at elevated temperature and pressure. As a result, the organic secondary products are oxidized essentially into $CO_2$ and $H_2O$ and the reaction gases are discharged through pipe 14. The waste liquor purified in this way is then returned to the hydrolysis stream 5.

Figure 1:
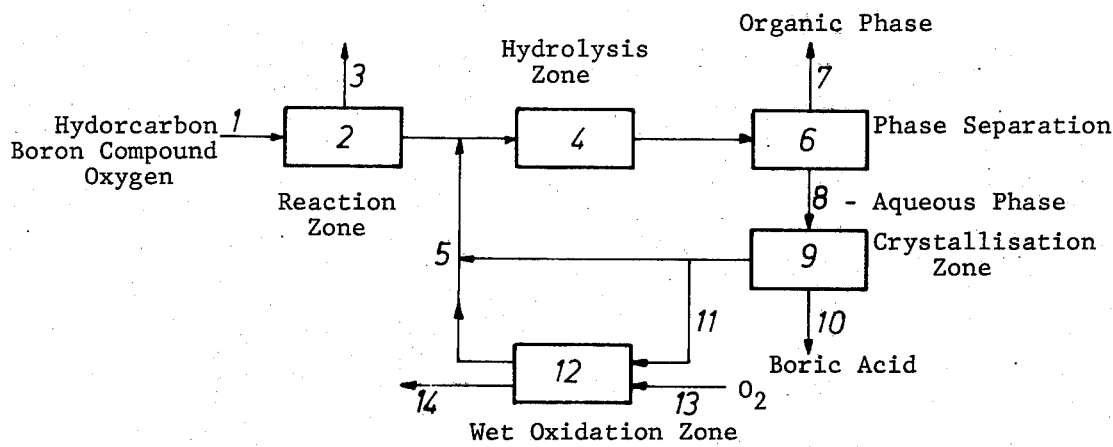
FIG. 1 is a diagrammatic flow diagram illustrating the manner in which the process of the invention can be carried out.
Figure 2:
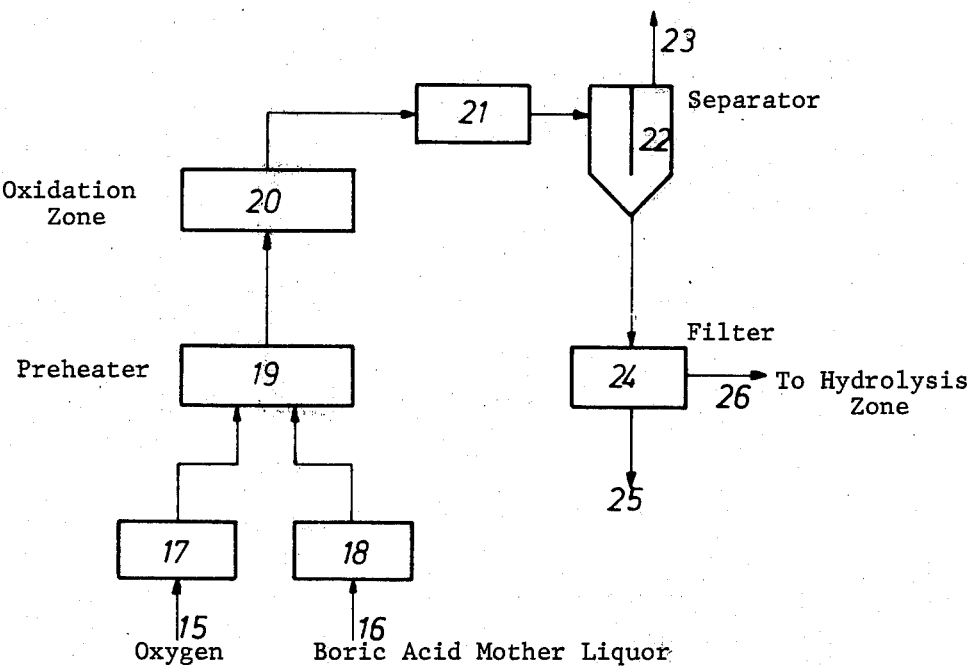
FIG. 2 is a further diagrammatic flow diagram illustrating the manner in which the wet oxidation stage of the invention can be carried out continuously.

The wet-oxidation stage carried out in the zone 12 is diagrammatically illustrated in FIG. 2 for continuous working. However, the process can of course also be carried out in batches. Oxygen-containing gas, for example air or an oxygen-containing fraction from an air-separation stage 15, is compressed to the required reaction pressure by the compressor 17 and, along with the component stream 16 of boric acid mother liquor delivered by the high-pressure pump 18, is introduced through a preheater 19 into the high-pressure reactor 20. After passing through the reaction zone, the gas-liquid mixture is cooled in a heat exchanger 21 and separated in the separator 22 into exhaust gas 23 and waste liquor. Any solids formed can be separated off in the filter 24. The waste liquor is returned to the hydrolysis stage 26. The solids are discharged through pipe 25.

The process stage illustrated in FIG. 2 indicate a number of known possibilities of variation. For example, the reaction gas and reaction liquid can be preheated together, for which purpose the reaction mixture issuing from the reactor can of course be used as a heating medium so that, conversely, the input also serves as a coolant for the separated component. To start the reaction and to start up the system, the preheater must also be heatable by another heating medium. In addition, the excess heat of reaction has to be dissipated in another subsequent condenser so that heat can be recovered to heat other systems, for example in the hydrocarbon oxidation process. The reaction stage 20 can have one or several stages. The reactor or reactors can be provided with a pressure tight stirrer or can obtain other fittings suitable for the favourable distribution of gases.

For recovering energy, the highly compressed exhaust gas 23 can be passed, for example, through a turbine which in turn transfers the energy to the compressor 17. The separation of solids, if any, in 24 can be carried out in a conventional manner, for example by means of a rotary filter, a hydrocyclone or a centrifuge.

The reaction conditions for the process according to the invention are variable within relatively wide limits. The reaction temperature can be from 200° to 370° C, although it is preferably in the range of from 270° to 350° C. The reaction pressure is preferably higher than the water-vapor pressure at the particular reaction temperature to ensure that water is kept in the liquid phase in at least such a quantity that the solubility of the ingredients of the boric acid mother liquor is not fallen below. Accordingly, the pressure can vary from 20 to 220 atms. and is preferably from 60 to 180 atms. It is also possible to use solid catalysts which can subsequently be recovered by filtration. These catalysts are well known, e.g., active carbon or oxides of vanadium, molybdenum or tungsten.

In order to oxidize the ingredients as completely as possible, molecular oxygen must be supplied to the wet-oxidation reaction in at least stoichiometric quantities. Although an excess of oxygen enables a higher conversion to be obtained, it also involves higher compression costs. In order completely to eliminate the water-soluble organic secondary products accumulating during oxidation of the hydrocarbons, the wet-oxidation stage can also be carried out with an incomplete conversion providing the component stream of boric acid mother liquor delivered to the wet-oxidation stage is increased in accordance with the lower conversion. As a rule, any displacement which this produces in the composition of the organic ingredients in the hydrolysis circuit does not have an adverse effect upon the process.

The process according to the invention is illustrated by, but by no means limited to, the following Examples. A boric acid mother liquor taken from a continuous-cycle installation in which cyclohexane is oxidized with air in the presence of metaboric acid to form a mixture of cyclohexanol and cyclohexanone by the process described earlier on, was used for the Examples. The boric acid mother liquor had the following composition and analytical data:

75% of water, 8.0% of orthoboric acid, approximately 17 % of organic constituents, corresponding to 9.25% of carbon, the COD (Chemical Oxygen Demand)-value amounts to 298mg of $O_2$/g. The method of determination of the COD-value is well known and, e.g., described in W. Leithe, Oesterreichische Abwasser-Rundschau, 2, (1970), page 25 - 28.

EXAMPLES 1 to 8; Batch Tests

An electrically heated 2 liter capacity fine-steel autoclave, equipped with a magnetic lift stirrer, gas inlet and reflux condenser, was used as the test apparatus. Compressed air was used as the oxidation gas. The exhaust gas was let off through a valve behind the reflux condenser and the quantity of exhaust gas was measured by a following rotameter. With the compressed-air valve open, the quantity of exhaust gas was regulated by the exhaust-gas valve and, with it, a required quantity of compressed air was indirectly adjusted. 825 g of boric acid mother liquor were introduced and heated to the required temperature with the exhaust-gas valve closed. The test pressure was then adjusted by means of the compressed-air valve. The stirrer operated at 50 lifts per minute. The test began by opening the exhaust-gas valve and adjusting the required quantity of exhaust gas. The test data are shown in Table 1 below. The conversion was calculated from the residual carbon content of the final sample. As can be seen from the Table, the carbon content of the boric acid mother liquor was reduced by from 43 to 91%.

Table 1:

| | Batch Test 1 - 8 | | | | |
|---|---|---|---|---|---|
| Test Number | Temperature °C | Pressure atms. | Exhaust gas Nl/h | Duration h | Conversion according to C% |
| 1 | 200 | 80 | 100 | 2.5 | 43 |
| 2 | 200 | 80 | 100 | 12 | 78 |
| 3 | 240 | 80 | 100 | 12 | 88 |
| 4 | 270 | 80 | 100 | 8.5 | 90 |
| 5 | 240 | 80 | 300 | 2.5 | 85 |
| 6 | 270 | 100 | 300 | 2.8 | 87 |
| 7 | 290 | 100 | 300 | 2.5 | 91 |
| 8 | 270 | 80 | 300 | 1 | 60 |

EXAMPLES 9 to 15: Continuous Tests

The test arrangement used in Examples 1 to 8 was additionally equipped with two submerged pipes. One of these pipes was used for introducing the fresh boric acid mother liquor by means of a metering pump, whilst the other was equipped with a valve and a descending condensor for letting off, venting and cooling the oxidized waste liquor. The exhaust gas was analysed for its CO, $CO_2$ and $O_2$-contents. The quantity of exhaust gas and, hence, ultimately the quantity of compressed air was measured in tests 9 to 12 in such a way that approximately 8% more of oxygen than required for complete oxidation was available. In test 13, a low conversion was deliberately aimed at by means of a deficit of air and a short residence time.

The tests were carried out as follows:

A certain quantity of mother liquor was introduced, the autoclave was closed and compressed air was introduced into it up to a pressure of 45 atms. The stirrer was adjusted to 50 lifts per minute. After heating, the test pressure and the quantity of exhaust gas were adjusted and the liquor metering pump was started up. Oxidized waste liquor was discharged from the autoclave at a rate commensurate with that at which liquor was pumped in. After a few hours, equilibrium prevailed in the system, recognizable from the constant analytical values of the waste-liquor samples. The conversion reached was calculated from the COD-values of the mother liquor used and the final sample. The test data and results are set out in Table 2:

Table 2:

| | Continuous Tests 9 - 15 | | | | | | |
|---|---|---|---|---|---|---|---|
| Test Number | 9 | 10 | 11 | 12 | 13 | 14 | 15 |
| Temperature ° C | 270 | 290 | 290 | 290 | 290 | 310 | 330 |
| Pressure (atms.) | 100 | 100 | 100 | 100 | 100 | 125 | 160 |
| Quantity introduced (ml) | 525 | 525 | 525 | 1000 | 525 | 870 | 800 |
| Throughput (ml/h) | 350 | 525 | 350 | 350 | 2500 | 1080 | 2000 |
| Residence time (h) | 1.5 | 1.0 | 1.5 | 2.9 | 0.21 | 0.8 | 0.4 |
| Quantity of exhaust gas (Nl/h) | 370 | 560 | 370 | 370 | 1300 | 1160 | 2130 |
| Conversion according to COD | 82% | 84% | 90% | 94% | 41% | 93% | 94% |
| o/oo solids | 0.9 | 1.5 | 0.8 | <0.1 | 30 | 0.2 | <0.1 |

In test 13, the relatively high solids component gave rise to considerable difficulties. The liquor-discharge valve was frequently blocked and could only be rinsed free again by a sudden, wide opening which gave rise to considerable pressure and quantitative fluctuations. In addition, the fittings of the autoclave were covered after only a few hours by a thin, tacky layer of resin, a condition which would give rise to considerable difficulties in the event of prolonged continuous operation.

In tests 9 to 12, 14 and 15, the small quantity of solids was readily filtered off. The final boric acid liquor accumulating could then be reused for hydrolysis without any disadvantages.

The residence times quoted were determined essentially by the parameters of the test apparatus and could be shortened by means of suitable technical measures.

What is claimed is:

1. In a process for oxidizing hydrocarbons wherein
   a. saturated $C_4$–$C_{20}$ hydrocarbons are reacted with a gas comprising molecular oxygen in the presence of a boron compound forming esters with alcohols formed from said hydrocarbons;
   b. the resulting reaction mixture containing at least one boric acid ester is hydrolyzed;
   c. the hydrolyzate is separated into a substantially organic component, from which the oxidation product is recovered, and into a substantially aqueous component, containing boric acid and water-soluble organic secondary products; and
   d. boric acid from the aqueous component is recycled to (a);

the improvement which comprises
   e. crystallizing boric acid from the aqueous phase to deposit therefrom the boric acid which is recycled to (a), thereby leaving a saturated aqueous mother liquor containing boric acid;
   f. oxidizing at least part of the residual saturated boric acid-containing mother liquor from (e) in the liquid phase with a gas comprising molecular oxygen at a temperature of at least 200° C and under a pressure sufficient to keep at least some of the water in the liquid phase so that the organic impurities contained in said mother liquor are oxidized to an extent of from about 41 to 94%; and
   g. recycling the resulting aqueous solution containing boric acid from step (f) to the hydrolysis of step (b).

2. Process of claim 1 wherein the gas for oxidation of the boric acid mother liquor in step (f) contains oxygen in an amount at least equal to the stoichiometric amount needed for combustion of the organic secondary products.

3. Process of claim 1 wherein the liquid-phase oxidation of step (f) is carried out at a temperature of from 200° to 370° C and under a pressure of from 20 to 220 atms.

4. Process of claim 1 wherein the liquid-phase oxidation of step (f) is carried out at a temperature of from 270° to 350° C and under a pressure of from 60 to 180 atms.

5. Process of claim 1 wherein the hydrocarbon is cyclohexane or cyclododecane.

6. The process of claim 1 wherein said organic impurities in step (f) are oxidized to an extent of at least 60%.

7. The process of claim 6 wherein said organic impurities in step (f) are oxidized to an extent of from about 70 to 80%.

* * * * *